United States Patent [19]
Reddy

[11] Patent Number: 5,945,365
[45] Date of Patent: Aug. 31, 1999

[54] STEREORIGID BIS-FLUORENYL METALLOCENES

[75] Inventor: Baireddy R. Reddy, Baytown, Tex.

[73] Assignee: Fina Technology, Inc., Dallas, Tex.

[21] Appl. No.: 08/651,839

[22] Filed: May 20, 1996

[51] Int. Cl.[6] .................................................... C08F 4/64
[52] U.S. Cl. ...................... 502/117; 502/152; 502/155; 526/127; 526/160; 526/943; 526/161; 556/11; 556/43; 556/53
[58] Field of Search ..................... 502/103, 117, 502/152, 155; 556/43, 53, 11; 534/15; 526/943

[56] References Cited

U.S. PATENT DOCUMENTS

| | | | |
|---|---|---|---|
| 5,036,034 | 7/1991 | Ewen | 502/117 |
| 5,155,080 | 10/1992 | Elder et al. | 502/152 |
| 5,191,132 | 3/1993 | Patsidis et al. | 585/375 |
| 5,328,969 | 7/1994 | Winter et al. | 526/127 |
| 5,329,033 | 7/1994 | Spaleck et al. | 556/53 |
| 5,334,677 | 8/1994 | Razavi et al. | 526/114 |
| 5,401,817 | 3/1995 | Palackal et al. | 526/127 |
| 5,436,305 | 7/1995 | Alt et al. | 526/160 |
| 5,451,649 | 9/1995 | Zenk et al. | 526/160 |
| 5,459,117 | 10/1995 | Ewen | 502/117 |

FOREIGN PATENT DOCUMENTS

| | | |
|---|---|---|
| 2067525 | 4/1992 | Canada . |
| 628565 | 12/1994 | European Pat. Off. . |

OTHER PUBLICATIONS

Chen et al, *Macromolecules*, "$C_{2v}$- and $C_2$-Symmetric ansa-Bis(fluorenyl)zirconocene Catalysts: Synthesis and α-Olefin Polymerization Catalysis," vol. 28, No. 16, (1995).
Vogel's *Textbook of Practical Organic Chemistry*, 4th Edition, 1978, pp. 671,755.
Newman et al, *J. Org. Chem.*, "The Synthesis of 4-Bromophenanthrene," vol. 34, No. 6, pp. 1904–1906 (1969).
Barker et al, *J. Chem. Soc.*, 3:6–Disubstituted Fluorenes. Part I. The Attempted Introduction of a 6:6'–Methylene Bridge Directly into 3:3'–Diaminodiphenyl and Some of its Derivatives, pp. 2034–2036 (1953).
Barker, et al, *J. Chem. Soc.*, 3:6–Disubstituted Fluorenes. Part II. The Preparation of 3:6–Diaminofluorene from Fluorene, and the Attempted Internuclear Cyclisation of Derivatives of 4:4'–Diaminodiphenylmethane, pp. 870–873 (1953).
Hawley's Condensed Chemical Dictionary, 11th Ed. Van Nostrand Reinhold, New York, 1987, pp. 89, 749.

*Primary Examiner*—David W. Wu
*Attorney, Agent, or Firm*—Jimmy D. Wheelington; M. Norwood Cheairs; William D. Jackson

[57] ABSTRACT

Metallocene catalyst components having bis-fluorenyl ligands of a staggered conformation and processes for the isotactic propagation of a polymer chain from ethylenically unsaturated monomers. The catalyst components comprise bridged bis-fluorenyl metallocenes characterized by the following formula:

$$X(F1Y_a)(F1'Z_b)MeQ_n \qquad (1)$$

wherein, F1 and F1' are fluorenyl groups which are interconnected by a structural bridge X to impart stereorigidity to the metallocene ligand, Me is a Group 3, 4, or 5 transition metal each Y is the same or different and is a hydrocarbyl or heterohydrocarbyl substituent at a distal position on the fluorenyl group, each Z is the same or different and is a hydrocarbyl or heterohydrocarbyl substituent at a distal position on the other fluorenyl group F1', and a and b are each independently 1 or 2. The relative locations of Y and Z on their respective fluorenyl groups are such that each is in a staggered position relative to a plane of symmetry through the ligand structure which contains the structural bridge. The substituent groups Y and Z are on opposed sides of this plane of symmetry to provide a staggered conformation to the ligand. One of the substituents Y and Z may take a form of a heterohydrocarbyl group with the other a hydrocarbyl group. Z may be a hydrocarbyl group and Y a heterohydrocarbyl group, specifically an alkyl and alkoxy group such as an oxymethyl group, or an amino group such as a dimethylamino group. Y and Z may be the same.

15 Claims, No Drawings

STEREORIGID BIS-FLUORENYL METALLOCENES

FIELD OF THE INVENTION

This invention relates to catalysts and processes for the production of isotactic alpha olefins and more particularly to bridged bis-fluorenyl metallocenes having staggered substituent groups which are effective as olefin polymerization catalysts.

BACKGROUND OF THE INVENTION

Syndiotacticity and isotacticity involve two broad classes of stereospecific structure formations which may be involved in the formation of stereoregular polymers from various monomer units. Syndiotactic polymers, such as syndiotactic polypropylene, have a stereochemical structure in which the monomeric units have an enantiomorphic configuration in which the methyl groups on the asymmetrical carbon atoms follow each other alternatively and regularly in the main polymer chain. In contrast to syndiotactic polymers, isotactic polymers generally are characterized as having the methyl groups on the repeating units with identical sequence configurations as contrasted with the alternating configurations of syndiotactic polymers. Such structures may be described by conventional and well-known graphical presentations, such as Fischer projection and corresponding NMR pentad sequences as disclosed, for example, in U.S. Pat. Nos. 5,334,677 to Razavi et al and 4,522,982 to Ewen. While isotacticity and syndiotacticity are useful in defining these two broad types of crystalline polymer configurations, alternatives of both are known in the prior art. For example, so-called stereoblock polymers, such as disclosed in the aforementioned '982 patent, may be involved. Also a specialized form of isotactic polypropylene in which alternative polymer units achieve a random asymmetricity can be formed as stereoblock polymers which can be formed, for example, of alternating isotactic blocks. Various monomers which can be stereospecifically propagated include the ethylenically unsaturated monomers such as $C_3$+alpha olefins, such as propylene and 1-butene; dienes, such as 1,3-butadiene; substituted vinyl compounds, such as vinyl chloride or vinyl aromatic compounds, e.g. styrene; and vinyl ethers, such as alkyl vinyl ethers, e.g. isobutylvinyl ether or even arylvinyl ethers. As indicated above, the most significant application of stereospecific polymerization is in the production of isotactic or syndiotactic polypropylene.

The catalyst systems useful in the formation of isotactic polyolefins include the racemic bis-indenyl compounds of the type disclosed in U.S. Pat. No. 4,794,096 to Ewen. Those useful in the propagation of syndiotactic polypropylene and like syndiotactic polymers include stereorigid metallocenes having different substituted cyclopentadienyl groups, e.g. bridged cyclopentadienyl fluorenyl ligands, as disclosed, for example, in U.S. Pat. No. 5,334,677 to Razavi et al and U.S. Pat. No. 5,155,080 to Elder et al. A variation of such cyclopentadienyl fluorenyl ligand structures, which are substituted so as to produce a lack of bilateral symmetry, are disclosed in U.S. Pat. No. 5,036,034 to Ewen to produce hemi-isotactic polypropylene.

While the foregoing structures can be generally characterized as having fluorenyl-cyclopentadienyl ligand structures, another class of compounds having bis-fluorenyl ligand structures are known in the art as useful in producing crystalline polymer structures involving isotactic or syndiotactic polymer chains. Thus, U.S. Pat. No. 5,401,817 to Palackal et al discloses silicon bridged bis-fluorenyl compounds in which one fluorenyl group is unsubstituted or symmetrically substituted and the other is a different fluorenyl radical which is unsubstituted or symmetrically substituted. Alternative ligand configurations are disclosed in Palackal et al in which only one fluorenyl group is involved, but at least one of the groups in the ligand structure, characterized in Palackal as being a silyl bridged sandwiched metallocene, must be a fluorenyl group. The substituents of the silyl bridge may be identical or different $C_1$–$C_{20}$ organo radicals, such as fluoro alkyl or aryl groups, alkyl groups, aryl groups, or alkylaryl groups. Characteristic of the symmetrical ligand structures disclosed in Palackal are 9-(2,7-di-t-butylfluorenyl)-9'-fluorenyldiphenylsilane and the corresponding 3–6 alkyl derivative. As is normally the case with such metallocene catalysts, the silyl bridged metallocenes of Palackal are employed in conjunction with a cocatalyst such as an alumoxane which may be used alone or in conjunction with a trialkyl aluminum.

Other examples of fluorenyl-based metallocenes are disclosed in U.S. Pat. No. 5,451,649 to Zenk et al. In Zenk et al, both bridged and unbridged metallocenes are disclosed. Particularly preferred in Zenk et al are bridged metallocenes containing at least one symmetrically substituted fluorenyl radical. Suitable symmetrically substituted fluorenyl groups include 2,7-di-alklyfluorenyls, the corresponding 3,6 and 1,8 derivatives and 2,3:6,6 and 3,4:5,6 dibenzofluorenyls. As disclosed in Zenk, the alkyl derivatives may range from 1 to 20 carbon atoms with 1 to 6 being preferred. Aryl substituents may range from 6 to 20 carbon atoms with 6 to 10 carbon atoms being preferred for unsubstituted aryls and 7 to 10 carbon atoms being preferred for aryl alkyl substituents. Various alpha olefins, disclosed as being suitable for polymerization by the Zenk et al catalysts, include ethylene, propylene, 1-pentene, 1-heptene, 1-octene, 1-decene and various alkyl and dialkyl substituted derivatives of such alpha olefins.

Similarly bridged and unbridged metallocenes derived from fluorenyl ligands are disclosed in Canadian Patent No. 2,067,524 to Alt et al. Here such bridged or unbridged compounds are said to be useful catalysts in the production of polymers such as crystalline and a noncrystalline polypropylene. For example, Alt et al discloses the use of 1,2-di(2-tert butyl fluorenyl)ethane zirconium dichloride to produce crystalline polypropylene. Various techniques are disclosed in Alt for the production of various alkyl substituted fluorenes from the correspondening carboxylic acid fluorenes. For example, as disclosed in Alt, 1-carboxylic acid fluorenone can be converted to 1-methylfluorene by a reaction route involving the intermediate 1-hydroxymethyl fluorenone. Similar reaction routes can be used to produce 1-isopropyl fluorene and 2-tert-butyl fluorene as well as 4-fluorenyl derivatives such as 4-methyl fluorene and 4-tert-butyl fluorene.

Yet another disclosure of bis-fluorenyl metallocene catalysts is found in U.S. Pat. No. 5,459,117 to Ewen. Ewen discloses various metallocenes including bis-fluorenyl metallocenes which are said to be useful in the catalysis of isotactic or syndiotactic polypropylene. The stereorigid metallocenes of Ewen are disclosed there as being "doubly-conformationally locked" with substituted metallocenes characterized as having $C_2$ or $C_s$ symmetry or pseudo-$C_2$ or $C_s$ symmetry. Such metallocene ligands are characterized as having bis(4,5-di-substituted fluorenyl) ligands with $C_2$ or pseudo-$C_2$ symmetry resulting in an isospecific catalyst and with a $C_s$ or pseudo-$C_s$ symmetry resulting in a syndiospecific catalyst. The catalyst ligand structures have dissimilar substituents at the 4 and 5 positions of the fluorenyl groups with $C_s$ (or pseudo-$C_s$) symmetry resulting when the 4,5 substituents of one fluorenyl group or sterically smaller than the corresponding substituents of the other fluorenyl group, and $C_2$ or pseudo-$C_2$ symmetry resulting when one fluorenyl group has substituents which are smaller and larger than substituents on the other fluorenyl group. Suitable substituent groups at the 4 and 5 positions on the fluorenyl groups are said to include $C_1$–$C_{20}$ hydrocarbyl groups including heterosubstituted groups such as silicon, phosphorus, boron and nitrogen derivatives which can be linear or branch chain, as well as various $C_3$–$C_{20}$ cyclohydrocarbyl groups and aryl or alkylaryl groups. The bridge structure in Ewen is described broadly as a $C_1$–$C_{20}$ alkyl and bridges incorporating silicon, germanium, phosphorous, boron and aluminum which may be substituted with alkyl or aryl groups.

Yet another group of bis-fluorenyl metallocenes characterized as having $C_{2v}$ or $C_2$ symmetry and their use as alpha olefin polymerization catalysts are disclosed in Chen et al, *Macromolecules*, "$C_{2v}$ and $C_2$-Symmetric ansa-Bis (fluorenyl)zirconocene Catalysts: Synthesis and α-Olefin Polymerization Catalysis," Vol. 28, No. 16, Jul. 31, 1995. Specifically disclosed in Chen et al are rac- and meso-ethylenebis[9-(1-methyl)fluorenyl]zirconium dichloride. In Chen et al a diastereomeric mixture of the rac- and meso-diastereomers was employed in a polymerization reaction to produce isotactic polypropylene having a relatively high mmmm pentad distribution. A somewhat similar disclosure is found in European Patent Application No. 628,565 to Patsidis et al. Here, metallocene structures characterized as bis-fluorenyl bridged sandwich-bonded metallocenes, having 1-methyl substitution as in the Chen et al article, were disclosed as useful with a mixture of racemic and meso isomers to produce isotactic polypropylene.

SUMMARY OF THE INVENTION

In accordance with the present invention, there are provided metallocene catalyst components having bis-fluorenyl ligands of a staggered conformation and processes for the use of such metallocenes in the isotactic polymerization propagation of a polymer chain derived from ethylenically unsaturated monomers which have three or more carbon atoms and/or are substituted vinyl compounds.

The catalyst components of the present invention comprise bridged bis-fluorenyl metallocenes which may be characterized by the following formula:

$$X(F1Y_a(F_1'Z_b)MeQ_n \quad (1)$$

In Formula (1), F1 and F1' are fluorenyl groups which are interconnected by a structural bridge X to impart stereorigidity to the metallocene ligand, each Y is the same or different and is a hydrocarbyl or heterohydrocarbyl substituent at a distal position on the fluorenyl group, each Z is the same or different and is a hydrocarbyl or heterohydrocarbyl substituent at a distal position on the other fluorenyl group F1', and a and b are each independently 1 or 2. The relative locations of Y and Z on their respective fluorenyl groups are such that each is in a staggered position relative to a plane of symmetry through the ligand structure which contains the structural bridge. The substituent groups Y and Z are on opposed sides of this plane of symmetry to provide a staggered conformation to the ligand. Further, with respect to Formula (1), Me is a transition metal from Groups 3, 4 and 5 of the Periodic Table of Elements. Q is a hydrocarbyl or halogen atom, and n is an integer within the range of 1–3.

The substituents Y and Z may be the same or different, and where they are different, one of the substituents may take a form of a heterohydrocarbyl group with the other a hydrocarbyl group. Z may be a hydrocarbyl group and Y a heterohydrocarbyl group, specifically an alkyl and alkoxy group such as an oxymethyl group, or an amino group such as a dimethylamino group.

Normally, Me will be selected from the group of scandium, titanium, zirconium, hafnium, vanadium and niobium in which case n will be 3 where Me is niobium or vanadium, 1 in the case of scandium and 2 in the case of the other three transition metals. Preferably, Me will be selected from the group consisting of titanium, zirconium and hafnium and more preferably zirconium.

Catalyst components embodying the present invention may further be characterized as metallocenes in accordance with the following structural formula:

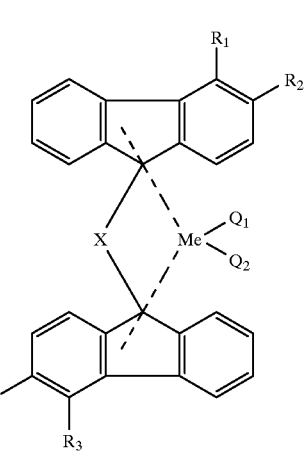

(2)

In Formula (2), $R_1$ and $R_2$ are each hydrogen or a hydrocarbyl or heterohydrocarbyl substituent provided that no more than one of $R_1$ and $R_2$ is hydrogen and provided similarly that no more than one of $R_3$ and $R_4$ is hydrogen. X and Me are as described above, but preferably Me is titanium, zirconium, hafnium and vanadium. $Q_1$ and $Q_2$ are identical or different and are a halogen atom, an alkyl group which may be linear or branched chained, containing from 1 to 20 carbon atoms, preferably 1 to 10 carbon atoms, an alkoxy group containing from 1 to 10 carbon atoms, an aryl group containing from 6 to 10 carbon atoms, or an aryloxy group containing from 6 to 10 carbon atoms. Preferred bridges for use in carrying out the present invention are silicon bridges or methylene or ethylene bridges although other bridge components incorporating germanium or tin, as are conventionally used in forming bridged metallocenes, may, of course, likewise be involved in the present invention.

The preferred catalyst component of the present invention is characterized by the formula:

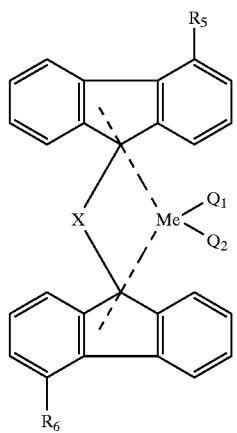

(3)

Here, $R_5$ and $R_6$ are each a hydrocarbyl or heterohydrocarbyl substituent as described above and X, Me, $Q_1$ and $Q_2$ may be characterized as described previously. Preferably, $R_5$ and R6 are each independently one of the following groups: $OCH_3$, $CH_3$, $N(CH_3)_2$, or isopropyl or tertiary butyl groups.

In yet a further aspect of the present invention, there is provided a method for the polymerization of an ethylenically unsaturated monomer to produce an isotactic polymer of the monomer. In carrying out the invention, there is provided a metallocene catalyst characterized by the formula:

$$X(F1Y_a)(F1'Z_b)MeQ_kP_l \quad (4)$$

wherein X, F1, F1', Y, Z, a, b, and Me are as described above, Q is a hydrocarbyl radical having from 1 to 10 carbon atoms or is a halogen, P is a stable non-coordinating or weakly coordinating anion, k is an integer having a value of from 1 to 3, and 1 is an integer having a value of from 0 to 2. The catalyst is contacted in a polymerization reaction zone with an ethylenically-unsaturated monomer containing at least three atoms under polymerization conditions to produce isospecific polymerization of the monomer. Specifically, the ethylenically-unsaturated monomer may take the form of a $C_3+$ alpha olefin, specifically propylene, 1-butylene, or 4-methyl-1-pentene, a vinyl aromatic such as styrene, or a substituted vinyl compound such as vinyl chloride.

DETAILED DESCRIPTION OF THE INVENTION

The present invention involves certain bridged metallocenes and their use as catalysts in isotactic polymer propagation. The term "bridged metallocene," as used herein in accordance with a normal art usage, denotes an organic coordination compound in which two cyclo-5 ligands (cyclopentadienyl or substituted cyclopentadienyl rings) are bridged together with a structural bridge to provide a stereorigid structure and which are bonded to a central metal ion which may be provided by a Group 3, 4 or 5 transition metal or metal halide, alkyl alkoxy, aryloxy or alkoxy halide aryl or the like. The term "molecular sandwich" is sometimes applied to such structure since the two cyclo $C_5$ ligand structures are oriented above and below the plane of the central coordinated metal atom. The structural bridge interconnecting the two $C_5$ ligand structures imparts stereorigidity to the metallocene complex to prevent rotation of the two cyclo $C_5$ ligand structures about their coordination axes with the transition metal atom.

Bis-fluorenyl metallocenes are metallocenes in which each of the cyclo $C_5$ ligand components is a fluorenyl group which may be substituted or unsubstituted. Bis-fluorenyl ligands may be characterized by the following structural formula in which the upper and lower fluorenyl groups are interconnected by a chemical bridge X as described previously.

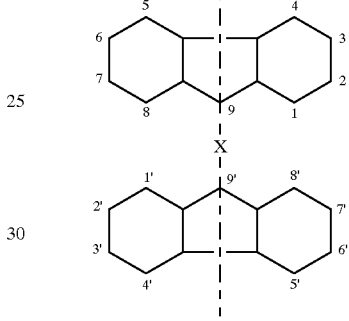

(5)

While numerous numbering schemes are known in the art, one conventional mode is to designate each of the "bridge head" carbon atoms as 9 and to number the non-conjugated carbon atoms in a sequence in which the directly proximal carbon atoms are numbered 1 and 8 and the directly distal carbon atoms are numbered 4 and 5. This numbering sequence is shown in the above Formula (5). It is also a conventional practice to refer to the symmetry of such ligand structures in terms of a line of symmetry which extends through the two bridge head carbon atoms and the structural bridge as shown by the vertical broken line of Formula (5). The present invention employs such bis-fluorenyl metallocene structures which are substituted in a manner to provide a staggered conformation to the ligand structure. In this staggered conformation, the top fluorenyl structure is substituted on one side of the broken line and the bottom fluorenyl structure is substituted on the other side of the broken line. Moreover, both substitutions occur at distal carbon atoms 3 and/or 4 and 3' and/or 4' in a manner to provide a structure which, in accordance with the present invention, can be characterized as the racemic equivalent of the typical isospecific ligand structure such as the enantiomorphic bis-indenyl structures of the aforementioned U.S. Pat. No. 4,794,096 to Ewen.

As disclosed, for example, in U.S. Pat. No. 5,225,500 to Elder et al, isotactic and syndiotactic polymer chains may be denominated by the so-called "Fischer" projection formula. In terms of the tertiary carbon atoms of successive monomer units of propylene, isotactic polypropylene may be characterized by the following structure:

(6)

Using Bovey's NMR nomenclature, for an isotactic pentad structure, structure 6 may be indicated as mmmm with each m representing a "meso" diad or pair of adjacent methyl groups on the same side of the plane of the polymer. Using the same Fischer projection format, the structure of a syndiotactic polymer maybe designated as

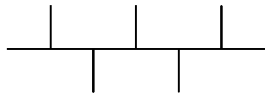

(7)

In NMR nomenclature, this pentad is described as rrrr in which each r represents a racemic diad, i.e., successive methyl groups on alternative sides of the plane of the polymer.

In the case of isotactic polypropylene, departures from the idealized case indicated by structure (6) are, of course, possible. One involves so-called "mistakes" in which an inversion occurs either regularly or randomly, for example, as in the so-called "hemi-isotactic polypropylene" as described in the aforementioned U.S. Pat. No. 5,036,034. Isotactic polypropylene may also take the form of so-called "stereoblocks," as disclosed for example in the aforementioned U.S. Pat. No. 4,794,096. Where occasional mistakes occur in conventional isotactic polypropylene, the result is occasional inversions which can be characterized as incorporating brief syndiotactic segments in a monomer chain which is predominantly isotactic as shown by the following structure.

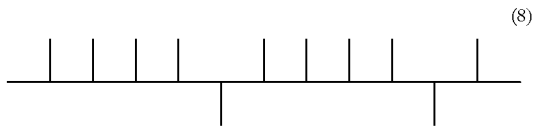

(8)

While the present invention is described in detail herein in regard to the polymerization of propylene to produce isotactic polypropylene, it is to be recognized that other ethylenically unsaturated monomers may be subjected to polymerization in accordance with the present invention. Such alpha olefins and other ethylenically unsaturated monomers are disclosed in the aforementioned U.S. Pat. Nos. 5,451,649 to Zenk et al and 5,459,117 to Ewen and include broadly organic molecules having a terminal vinyl group, including various alpha olefins, in addition to propylene, such as 1-butene, 1-pentene, 1-hexene, 4-methyl-1-pentene and the like; vinyl halides including vinyl fluoride, vinyl chloride, and the like; vinyl arenes including styrene, alkylated styrenes, halogenated styrenes, haloalkylated styrenes and the like; dienes such as 1,3-butadiene and isoprene (i.e. 1,2-addition).

The staggered metallocenes of the present invention usually will be employed as homogenous catalysts although it is to be recognized that such metallocenes may also be employed as heterogenous catalysts, i.e. as supported catalysts on a suitable insoluble particulate support. Suitable configurations for achieving a supported metallocene catalyst may be employed in the present invention. For example, the protocol disclosed in U.S. Pat. No. 5,422,325 to Jejelowo et al may be followed. Alternatively, advantage may be taken of the use of bridging groups which include ionic units or hydrocarbyl groups which can be integrated into a support structure, as disclosed, for example, in the aforementioned U.S. Pat. No. 5,459,117 to Ewen. Suitable bridging units can include ionic units, such as $B(C_6F_5)_2$, and $Al(C_6F_5)_2$, and the like and $R_2C$, $R_2Si$, $R_4Et$, $R_6Pr$, and the like where R can be any hydrocarbon, cyclic hydrocarbon, cyclic or linear hydrocarbons bearing another organometallic catalyst or carbonates, etc. Such bridges can be $C_2$ or $C_3$ or other bridges which form the backbone of polymeric supports (e.g. the atactic, syndiotactic and isotactic polymers from vinyl-indene and 9-vinyl-fluorene etc.) as well as functionalized polystyrene precursors and other polymers with terminal or branched boron or Al functional groups which are bonded to the catalysts, e.g., in zwitterionic form. For further consideration of suitable configurations to achieve heterogenous metallocene catalysts in accordance with the present invention reference may be had to the aforementioned U.S. Pat. No. 5,422,325 to Jejelowo et al and U.S. Pat. No. 5,459,117 to Ewen, the entire disclosures of which are incorporated by reference.

Further, while used as homogenous or heterogenous catalysts, the metallocenes of the present invention will be employed in conjunction with a suitable cocatalyst which can be generally characterized by organo-metallic compounds of metals of Groups IA, IIA and IIIB of the Periodic Table of Elements. As a practical matter, organoaluminum compounds are normally used as cocatalysts in polymerization reactions. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride and the like. Other examples of known cocatalysts include the use of a stable non-coordinating counter anion techniques such as disclosed in U.S. Pat. No. 5,155,080, e.g. using triphenyl carbenium tetrakis(pentafluorophenyl)boronate. Another example would be the use of a mixture of trimethylaluminum and dimethylfluoraluminum such as disclosed by Zambelli et, *Macromolecules,* 22, 2186 (1989). In such processes the metallocene or the cocatalyst can be employed on a solid insoluble support.

A currently preferred co-catalyst is an aluminoxane. Such compounds include those oligomeric or polymeric compounds having repeating units of the formula:

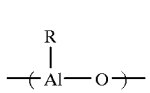

(9)

where R is an alkyl group generally having 1 to 5 carbon atoms. Aluminoxanes, also sometimes referred to as poly (hydrocarbyl aluminum oxides), are well known in the art and are generally prepared by reacting an organo aluminum compound with water. Alumoxanes may be either linear polymers or they may be cyclic, as disclosed for example in U.S. Pat. No. 4,404,344.

The currently preferred cocatalyst, prepared either from trimethylaluminum or triethylaluminum, is sometimes referred to as poly (-methyl aluminum oxide) and poly (ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

As noted previously with respect to the numbering system shown by Formula (5), the fluorenyl groups are substituted at the 3 and/or 4 position and the 3' and/or 4' position to provide a staggered metallocene ligand as characterized by the following structural Formula (2) as follows:

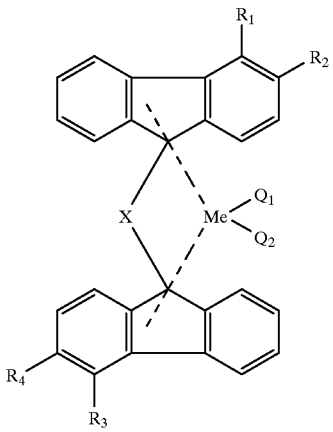

(2)

wherein $R_1$, $R_2$, $R_3$, $R_4$, X, Me, and $Q_1$ and $Q_2$ are as described previously. Preferably, $R_1$ and $R_3$ are substitutent groups, i.e. the metallocene ligand is substituted at the 4 and 4' positions without regard to substituent groups which may occur at other positions on the metallocene ligand structure. Specifically, such metallocenes may be substituted also at the C1, C-2 or 3 positions. The preferred metallocene structure will be as indicated by Formula (3) as follows with the only substituents occuring at the 4, 4' positions on the ligand structure:

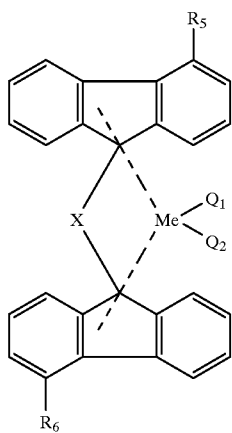

(3)

Here, it is preferred that $R_5$ and $R_6$ are methyl, methoxy, dimethylamino, isopropyl or tertiary butyl groups.

The structural bridge X can take the form of any suitable bridging structure, as disclosed, for example, in the aforementioned Palackal '817 patent, Razavi '677 patent, Zenk '649 patent or Ewen '117 patent. Suitable bridge moieties include hydrocarbyl or heteroatom containing alkylene radicals containing 1 to 20 carbon atoms, especially 2 to 20 carbon atoms; germanium; silicon; phosphorus; boron; aluminum; tin; oxygen; nitrogen; and the like. The bridge can be a cyclic hydrocarbyl structure, such as cyclopentylidene, adamantylidene, cyclohexenylidene, cyclohexylidene, indenylidene and the like. The bridge when hydrocarbyl can be a hydrocarbyl ethylene radical of the formula:

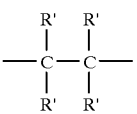

(10)

wherein each R' is the same or different and is selected from hydrogen or hydrocarbyl radical; or the divalent methylene radical —CR'$_2$—, wherein each R' is the same or different and is selected from methyl, phenyl and hydrogen radicals; or can be aromatic in nature, such as a phenyl-substituted alkylene. The preferred bridges are hydrocarbyl or heteroatom containing alkylene radicals having 1 to 20 carbon atoms.

In a preferred embodiment of the invention, the structural bridge X can be characterized by the structure wherein X is one of the following structures:

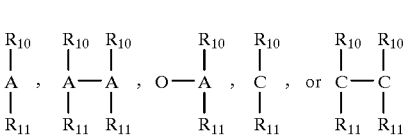

(11)

wherein A is silicon, germanium, tin, $R_{10}$ and $R_{11}$ are the same or different and are a hydrogen atom, a halogen atom, an all group containing one or two carbon atoms or an aryl group containing 6–10 carbon atoms.

Preferably, X will take the form of a silicon bridge or a methylene or ethylene bridge. Such silicon bridge metallocenes include those having dimethylsilyl bridge and diphenylsilyl groups. Preferred methylene bridges are the isopropylidene (dimethyl methylene) bridges.

As noted previously, the conventional metallocene configuration for the isospecific propagation of an alpha olefin such as propylene to produce a crystalline polymer is the enantiomorphic configuration offered by racemic-bisindenyl ligands. Corresponding meso-bisindenyl ligands produce atactic polymer. The bisfluorenyl ligands can be used to produce isotactic as well as syndiotactic polypropylene. Thus, the aforementioned U.S. Pat. No. 5,459,117 to Ewen discloses the production of syndiotactic polypropylene with bis(4,5 disubstituted fluorenyl) ligands when the ligand structures have so-called $C_s$ or pseudo-$C_s$ symmetry. This, of course, corresponds to the well-known configuration of metallocene ligands having bilateral symmetry for the production of syndiotactic polypropylene. The so-called $C_2$ or pseudo-$C_2$ is present because of 4,5 disubstituted fluorenyl ligands having large and small substituents on the same fluorenyl group. The result disclosed in the Ewen patent is isotactic polymer propagation. The requirement for 4,5 substituents on the ligand structure in order to achieve isotactic polymer propagation offers a number of disadvantages or potential difficulties.

The 4,5 disubstituted fluorenes are difficult to synthesize because of the steric hindrance between the two substituents in the 'mouth' region of fluorene (Agr. Biol. Chem., 26, 401 (1962). The substituents in the 4,5 positions are present in the most-crowded portion of a fluorene molecule. The separation of meso- isomers from the rac- isomers is also expected to be difficult (see *Macromolecules*, 28, 5339 (1995)). It is anticipated that the activity and polymer molecular weight production of 4,5- disubstituted bisfluorenyl complexes will be low due to the severe crowding in the "mouth" region of fluorene which also is the site of a portion of the monomer while being coordinated at the metal center during polymerization.

The present invention provides for catalyst systems which involve easily synthesizable fluorenes containing substituents only at the C3- and/or C4- positions, preferably at the C4-position, with or without substituents at C1-, C2- or C3- positions. Bridged bisfluorenyl metallocene systems containing only one substituent in the critically important "mouth" region of the fluorenes provide enough open space for the monomer coordination at the metal center and at the same time provide for tacticity differentiation of the monomer insertion to obtain isospecific polymers.

The metallocene catalysts of the present invention can be produced by following synthesis techniques known in the prior art. A suitable catalyst synthesis generally involves the following multi-step synthesis sequence: a) preparation of the substituted fluorene; b) preparation of the ligand; and c) preparation of the metallocene. Substituted fluorenes can be prepared according to methods found in the published literature whenever such fluorenes are not commercially available.

The 4-substituted fluorenes can be synthesized starting from the commercially available precursors using standard organic methods for functional group transformations described in the literature. Thus, 4-methyl fluorene can be prepared from 4-fluorene carboxylic acid by reaction with lithium aluminum hydride in etheral solvents, as described in the aforementioned Canadian Patent No. 2,067,525. The resulting 4-hydroxymethylfluorene can be reduced further to 4-methylfluorene with molecular hydrogen in the presence of a catalyst containing palladium on carbon. Conversion of commercially available 4-hydroxyfluorene to 4-methoxyfluorene can be accomplished by reaction with dimethylsulfate in dimethylsulfoxide in the presence of aqueous sodium hydroxide as described in Vogel's *Text Book of Practical Organic Chemistry,* 4th Edition, 1978, p. 755. Synthesis of 4-aminofluorene from fluorene-4-carboxylic acid can be carried out using the procedure described in *J. Org. Chem.,* 34, 1905 (1969). The 4-aminofluorene is coverted to 4-dimethylaminofluorene using trimethylphosphite according to the procedures described in *J. Chem. Soc.,* 2034 (1953); *J. Chem. Soc.,* 870 (1954) and Vogel's Text Book of *Practical Organic Chemistry,* 4th Edition, 1978, p. 671.

The present invention provides a substantial departure from the conventional wisdom followed by the Ewen '117 patent to achieve isotactic polymer propagation through an enantiomorphic site-control mechanism achieved by 4 substitution of the fluorenyl groups, in contrast with the complex 4,5 disubstituted fluorenyl groups of the prior art. The following examples illustrate the synthesis of ligands containing identically substituted fluorenes and differently substituted fluorenes containing different bridges as well as of a staggered metallocene in accordance with the present invention exemplified by the synthesis of racemic dimethylsilyl bis(4-methoxyfluorenyl) zirconium dichloride.

The following characterizes the procedure for the synthesis of a ligand containing identically substituted fluorene. Here, a dry, three necked flask equipped with a pressure equalized funnel, gas-inlet tube, rubber septa and a stirring bar is assembled in a dry box and charged with 30 ml of a tetrahydroforan (THF) solution of dichlorodimethylsilane (1.8 g, 13 mmol). The stirred solution is cooled to −78° C., and an ice-cold THF solution (30 ml) of 4-methoxy-fluorenyl lithium (5.1 g, 26 mmol) is added dropwise over a period of 30–40 min. The temperature is gradually raised to room temperature and stirred at this temperature for 24 h. The solvent is removed under vacuum. The residue is extracted with dry hexane and filtered under dry and inert atmosphere. Solvent is removed from the filtrate. The purity of the solid is checked by gas chromatography and $^1$H NMR. The solid of greater than 90% purity is used in the next step.

The following exemplifies the synthesis of an ethylene bridged ligand, namely ethylene bis(4-methoxyfluorene). A solution of n-butyllithium in hexane (1.6 M, 18 mmol) is added to a solution of 4-methoxyfluorene (3.0 g, 18 mmol) in anhydrous THF (30 ml) kept at 0° C. This mixture is stirred for one hour. The resulting solution is cooled to −78° C., and a solution of 1,2-dibromoethane (1.7 g, 9 mmol) in dry THF (20 ml) is added and stirred at −78° C. for 2 h. The temperature is gradually raised to 0° C. and then to room temperature and stirred overnight. Dilute hydrochloric acid is added, and the aqueous layer is extracted with three portions of ether. The organic layer is washed with saturated brine and dried over anhydrous sodium sulfate. Removal of the solvents gives a light yellow solid in 80–90% yield.

The following example represents the synthesis of silicon bridged ligand, namely dimethylsilyl (4-methoxyfluorenyl) (4-methylfluorenyl)silane, from the substituted fluorenes prepared as above. A hexane slurry of 4-methylfluorenyl lithium, prepared by the addition of n-butyllithium (1.6 M, 9.1 mmol) in hexane to a solution of 4-methylfluorene (1.62 g, 9 mmol) in hexane (30 ml) at room temperature, is cannulated at room temperature into a solution of dimethyldichlorosilane 3.5 g (26 mmol) in dry hexane (75 ml). The resulting mixture is stirred at room temperature for 4 hours, and the reaction mixture is filtered through dry, Analytical Grade Celite. The solvent and unreacted dichlorodimethylsilane are removed under vacuum. The resulting residue is redissolved in hexane, and a hexane slurry of 4-methoxyfluorenyllithium, prepared by the addition of n-butyllithium (1.6 M, 9.1 mmol) in hexane to a solution of 4-methoxy fluorene (1.76 g, 9 mmol) in hexane (30 ml), is added. The resulting heterogeneous mixture is stirred overnight and filtered through dry, Analytical Grade Celite. The filtration residue is washed with additional hexane and all of the filtrates are combined. Solvent is removed from the filtrate, and residual solid is recrystallized from hexane to obtain the ligand suitable for the next step involving the formation of dilithium salt followed by reaction with the halide of the transition metal exemplified by zirconium tetrachloride.

Two alternative procedures are available for the preparation of the metallocene, as exemplified by the following procedures for the synthesis of rac-dimethylsilyl bis(4-methoxyfluorenyl)zirconiumdicholoride.

Procedure 1

Dimethyl bis(4-methoxyfluorenyl)silane (3 g, 6.7 mmol) is dissolved in anhydrous diethyl ether (120 ml) and 2.2 equivalents of methyllithium (1.4 M) in ether is added at room temperature. The reaction mixture is stirred about one-half day at room temperature and the stirring is stopped. The solvent is decanted and the residue is washed with one portion of anhydrous pentane and the supernatant is decanted such that a small amount of solvent is left behind. A pentane slurry of zirconium tetrachloride (1.62 g, 7.0 mmol) is cannulated in and stirred at room temperature for several hours. The solvent is decanted from the reaction mixture and the residue is washed with dry hexane and the solid dried under vacuum. The product is dissolved in anhydrous methylene chloride and filtered. The filtrate is concentrated, and hexane is added slowly until crystallization is just initiated. The mixture is gradually cooled to 0° C. and then to −20° C. The precipitated solid is filtered and further crystallized until pure rac- isomer (by HNMR) is obtained for use in polymerization reactions as described below.

Procedure 2

The above procedure is repeated with the following changes. Subsequent to the addition of methyllithium during the dianion formation, anhydrous tetrahydrofuran (10 ml) is added. The mixture is stirred for about one-half day. The solvents are then removed under vacuum to obtain the dark colored dianion of the ligand. This solid is washed with three portions of dry hexane making sure that all the solid is completely suspended in the solid during the washing procedure. The rest of this procedure is similar to that described in Procedure 1.

The polymerization may be carried out by any suitable procedure as exemplified by the bulk polymerization and slurry polymerization procedures identified below as Procedures A, B and C.

Polymerization

Procedure A (Bulk Polymerization):

One milligram of the metallocene is dissolved in 5 ml MAO solution in toluene (10 wt % Al), transferred to a stainless steel sample cylinder, and charged with 400 ml of propylene into an autoclave reactor containing one liter propylene stirring at room temperature. The catalyst is prepolymerized in situ by heating the reactants to 60° C. within 5 minutes. After stirring at 60° C. and reactor pressure of 350–400 psi, the polymerization is terminated by rapidly venting the unreacted monomer and opening the reactor to the air. The contents of the reactor are dried in a vacuum oven at 50° C. for 2 h prior to anlaysis.

Procedure B (Slurry Polymerization)

The metallocene is dissolved in the reactor in 2.5 ml MAO solution. Another 2.5 ml MAO solution are added to 500 ml anhydrous toluene thermostated at 30° C. with 100 psi propylene in a stainless autoclave magnedrive reactor. The catalyst solution is transferred to a sample cylinder and charged into the reactor. The contents of the reactor are stirred at 30° C. for one hour and at the end of this time, the polymerization is terminated by venting the monomer and opening the reactor to air. Several hundred milliliters of methanol/4 N HCl solution is added; the precipitated polymer is collected on a filter funnel and dried in a vacuum oven prior to analysis.

Procedure C

Bulk polymerization of 1.4 Liters of propylene similar to Method A is done with the exception that no MAO is used. Instead, triphenyl carbenium tetrakis(pentafluorophenyl) boronate is used as an ionizing agent to ionize the neutral metallocene and form an ion pair with the metallocene cation. Triethylaluminum (0.66 mmol) is dissolved in toluene and is added to a 2 Liter Zipperclave reactor under 5 psi of nitrogen. One liter of propylene is condensed into the reactor. The mixture is stirred for 10 minutes at 1200 rpm. Triphenylcarbenium tetrakis(pentafluorophenyl) boronate (25 mg) is dissolved in 10 ml toluene. The metallocene (2.5 mg) is dissolved in 10 ml toluene. The two solutions are mixed for 5 minutes at room temperature. The catalyst solution is charged into the reactor from a stainlesssteel bomb along with 400 ml propylene. The reactor contents are stirred at 60° C. for 60 minutes, and the polymerization is terminated as described before.

As indicated by the foregoing, the metallocene compounds of the present invention may be employed in the isotactic polymer propagation of an ethylenically unsaturated monomer using various bulk or continuous polymerization procedures such as are well known in the prior art. While the invention will perhaps find its greatest application in the polymerization of $C_3$ +alpha olefins, particularly propylene, it may also be used in the polymerization of other ethylenically unsaturated monomers, including vinyl aromatics and heterovinyl compounds such as vinyl chloride. A cocatalyst, such as a trialkylaluminum, specifically triethylaluminum or trimethylaluminum, normally will be employed. Such cocatalysts effectively function as scavengers in the course of the polymerization procedure. Other suitable such cocatalysts include alkylaluminum halides, principally the chlorides, such as dialkylaluminum chloride and alkylaluminum dichloride, specifically, ethylaluminum dichloride and diethylaluminum chloride.

In carrying out the polymerization procedure of the present invention, the staggered metallocene introduced into the polymerization reaction zone may be characterized broadly by the formula:

$$X(F1Y_a(F1'Z_b)MeQ_kP_l \qquad (4)$$

wherein X, F1, F1', Y, Z, a, b, and Me are as described above, Q is a hydrocarbyl radical having from 1 to 10 carbon atoms or is a halogen, P is a stable non-coordinating or weakly coordinating anion, k is an integer having a value of from 1 to 3, and 1 is an integer having a value of from 0 to 2. The catalyst is contacted in a polymerization reaction zone with an ethylenically-unsaturated monomer containing at least three atoms under polymerization conditions to produce isospecific polymerization of the monomer. Specifically, the ethylenically-unsaturated monomer may take the form of a $C_3$+ alpha olefin, specifically propylene, 1-butylene, or 4-methyl-1-pentene, a vinyl aromatic such as styrene, or a substituted vinyl compound such as vinyl chloride.

Preferably, Me will be selected from the group consisting of titanium zirconium, hafnium and vanadium in which case k will be 1 or 2. In the foregoing formula where 1 is 1 or 2, it will be recognized that the metallocene catalyst can be characterized as a so-called "cationic" metallocene. Following the nomenclature here, the non-coordinating anion may be of any suitable type such as disclosed in the aforementioned U.S. Pat. No. 5,155,080 to Elder et al. Particularly preferred cationic metallocenes are those in which the anions indicated by P are fluorophenyl boronates. By way of example, anions P include tetrakis(pentafluorophenyl) boronate [BPh*$_4$]− tris (pentafluorophenyl)phenyl boronate [B(Ph*$_3$)(Ph)] and tris(pentafluorophenyl)4-trimethylsilyl-2,3,5,6-tetrafluorophenyl boronate [B(Ph*$_3$)(TMSPh*)]. An example of the formation of such cationic metallocenes is illustrated in the previous example in which triphenylcarbenium tetrakis(pentafluorophenyl) boronate is used as an ionizing agent with the neutral metallocene precursor. Other suitable non-coordinating anions are disclosed in the aforementioned U.S. Pat. No. 5,155,080 to Elder et al and also in European Patent Applications 277003 and 277004. Such anions include [W(PhF$_5$)]−, [MoPhF$_5$)]− (wherein PhF$_5$ is pentafluorophenyl), [ClO$_4$]−, [S$_2$O$_6$]−, [PF$_6$]−, [SbR$_6$]−, [AlR$_4$]− (wherein each R is independently, Cl, a $C_1$–$C_5$ alkyl group preferably a methyl group, an aryl group, e.g. a phenyl group or substituted phenyl group, or a fluorinated aryl group.) For further descriptions on the subject of such anions, reference is made to the aforementioned U.S. Pat. No. 5,155,080 and also European Patent Applications 277003 and 277004, the entire disclosures of which are incorporated herein by reference. The preferred boronate derivatives may be prepared from neutral metallocenes by techniques as disclosed in the aforementioned U.S. Pat. No. 5,387,568 to Ewen et al, the entire disclosure of which is incorporated herein by reference.

Where the value of 1 in the above-mentioned formula is zero, it will also be desirable to employ a catalyst such as TEAL. Here, since the metallocene is a so-called "neutral" metallocene, it will also be desirable to use aluminoxane materials such as described previously in addition to the alkylalumin or alkylaluminum chloride cocatalyst. Where 1 is 1 or 2, indicating the presence of a stable, non-coordinating anion, an aluminoxane is unnecessary and normally will not be employed. The TEAL or other such cocatalyst should, of course, be employed here.

Having described specific embodiments of the present invention, it will be understood that modifications thereof may be suggested to those skilled in the art, and it is intended to cover all such modifications as fall within the scope of the appended claims.

What is claimed:

1. A catalyst component useful in the polymerization of olefins comprising a metallocene characterized by the general formula:

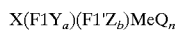

wherein:

F1 and F1' are fluorenyl groups of a metallocene ligand;

X is a structural bridge imparting stereorigidity by interconnecting the fluorenyl groups;

Y is a hydrocarbyl or heterohydrocarbyl substituent mono substituted at a distal position on the fluorenyl group F1;

Z is a hydrocarbyl or heterohydrocarbyl substituent mono substituted at a distal position on the fluorenyl group F1' at a location transverse of the plane of bilateral symmetry containing X from the group Y to provide a staggered conformation to said ligand wherein Y and Z are different and at least one of Z and Y is a heterohydrocarbyl group;

a and b are each independently 1 or 2;

Me is a Group 3, Group 4, or Group 5 metal from the Periodic Table of Elements;

each Q is independently a hydrocarbyl radical or a halogen atom; and n is an integer having a value within the range of 1–3.

2. The catalyst component of claim 1 wherein Z is a hydrocarbyl group and Y is a heterohydrocarbyl group.

3. The catalyst component of claim 2 wherein Y is an alkoxy group or an amino group.

4. The catalyst component of claim 1 wherein Me is selected from the group consisting of scandium, titanium, zirconium, hafnium, vanadium and niobium.

5. The catalyst component of claim 4 wherein Me is selected from the group consisting of titanium, zirconium and hafnium.

6. The catalyst component of claim 5 wherein Me is zirconium.

7. The catalyst component of claim 1 wherein Me is titanium, zirconium, hafnium or vanadium; Y and Z are each from the group R, as defined below, appearing respectively on at least one of the 3 and 4 carbon atoms of the fluorenyl group F1 and at least one of 3' and 4' carbon atoms to provide a substituted bisfluorenyl metallocene characterized by the following structural formula:

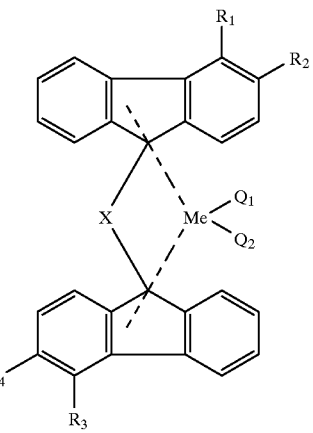

wherein:

$R_1$ and $R_2$ are each hydrogen or a hydrocarbyl or heterohydrocarbyl substituent provided that no more than one of $R_1$ and $R_2$ is hydrogen;

$R_3$ or $R_4$ are each hydrogen or a hydrocarbyl or heterohydrocarbyl group provided that no more than one of $R_3$ and $R_4$ is hydrogen and that at least one of the substituent $R_3$ and $R_4$ which is not hydrogen is different from at least one of the substituents $R_1$ and $R_2$ which is not hydrogen;

X is a structural bridging group;

Me is titanium, zirconium, hafnium or vanadium;

$Q_1$ and $Q_2$ are identical or different and are a halogen atom, an alkyl group containing from 1 to 20 carbon atoms, an alkoxy group containing from 1 to 10 carbon atoms, an aryl group containing from 6 to 10 carbon atoms or an aryloxy group containing from 6 to 10 carbon atoms.

8. The catalyst component of claim 7 wherein X is a structural bridge characterized by the formula:

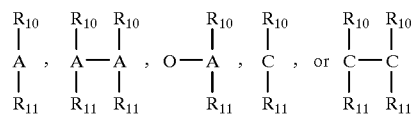

wherein:

A is silicon, germanium, tin;

$R_{10}$ and $R_{11}$ are the same or different and are a hydrogen atom, a halogen atom or an alkyl group containing one or two carbon atoms or an aryl group.

9. The catalyst component of claim 8 wherein X is a silicon bridge or is a methylene or ethylene bridge.

10. The catalyst component of claim 9 wherein X is an isopropylidene group or a dimethylsilyl group.

11. A catalyst component useful in the polymerization of olefin comprising a substituted bisfluorenyl metallocene characterized by the structural formula

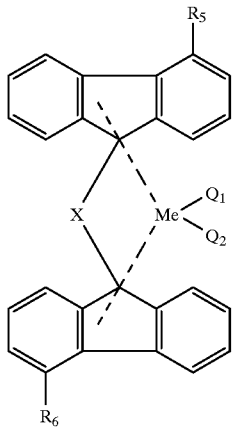

wherein:

$R_5$ and $R_6$ are different and are each a hydrocarbyl or heterohydrocarbyl substituent;

X is a structural bridging group;

Me is titanium, zirconium, hafnium and vanadium; and $Q_1$ or $Q_2$ are identical or different and are a halogen atom, an alkyl group attaining from 1 to 10 carbon atoms, an alkoxy group containing from 1 to 10 carbon atoms, an aryl group containing from 6 to 10 carbon atoms or an aryl oxy group containing from 6 to 10 carbon atoms.

12. The catalyst component of claim 11 wherein $R_5$ and $R_6$ are selected from the group consisting of $OCH_3$, $CH_3$, $N(CH_3)_2$, isopropyl and tert-butyl.

13. The catalyst component of claim 11 wherein $R_5$ is $N(CH_3)_2$ and $R_6$ is $CH_3$.

14. The catalyst component of claim 12 wherein $R_5$ is $OCH_3$ and $R_6$ is $CH_3$ or $N(CH_3)_2$.

15. The catalyst component of claim 14 wherein $R_6$ is $N(CH_3)_2$.

* * * * *